US006312661B1

(12) United States Patent
Reubi

(10) Patent No.: US 6,312,661 B1
(45) Date of Patent: Nov. 6, 2001

(54) METHOD FOR THE DETECTION AND LOCALIZATION OF DUCTAL EXOCRINE PANCREAS TUMOURS

(75) Inventor: Jean-Claude Reubi, Wabern (CH)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/355,869

(22) PCT Filed: Feb. 2, 1998

(86) PCT No.: PCT/US98/01964

§ 371 Date: Aug. 3, 1999

§ 102(e) Date: Aug. 3, 1999

(87) PCT Pub. No.: WO98/33531

PCT Pub. Date: Aug. 6, 1998

(30) Foreign Application Priority Data

Feb. 3, 1997  (EP) .................................................. 97200297

(51) Int. Cl.[7] .............................. A61K 51/00; A61B 5/055
(52) U.S. Cl. ....................... 424/1.69; 424/1.41; 424/9.34; 424/9.341
(58) Field of Search .................................. 424/1.69, 1.41, 424/9.3, 9.34, 9.341, 9.36; 514/2, 6, 14, 15, 16, 17, 21

(56) References Cited

FOREIGN PATENT DOCUMENTS

95/22341 * 8/1995 (WO) ............................ A61K/38/00

OTHER PUBLICATIONS

Ishizuka et al., Annal of Surgery, 217, pp,. 439–446, 1993.*

* cited by examiner

Primary Examiner—Michael G. Hartley
(74) Attorney, Agent, or Firm—Rothwell, Figg, Ernst & Manbeck

(57) ABSTRACT

The invention relates to a method of detecting and localizing malignant tumors and their metastases in tissues, which in healthy condition and in non-neoplastic conditions of chronic inflammation do not contain substantial quantities of neurotensin-receptors, in the body of a human being, which comprises: (i) administering to said being a composition comprising, in a quantity sufficient for external imaging, a radiolabelled peptide selected from the group consisting of neurotensin (NT), NT-receptor agonists. NT-receptor antagonists, NT analogues and NT derivatives; and thereupon (ii) subjecting said being to external imaging, by radioactive scanning or by magnetic resonance imaging, to determine the targeted sites in the body of said being. The invention further relates to a method for the therapeutic treatment of said malignant tumors by administration of the above-defined peptide, labelled for this purpose, and to the differential-diagnostic assessment and detection of a specific tumor type (i.e. ductal exocrine pancreatic carcinoma) of the pancreas. The invention also relates to a pharmaceutical composition to be used for detection, a pharmaceutical composition to be used for therapy and to a kit for preparing a radiopharmaceutical composition.

35 Claims, 2 Drawing Sheets

SEQUENCE LISTING

<160> NUMBER OF SEQ ID NOS: 3

<210> SEQ ID NO 1
<211> LENGTH: 13
<212> TYPE: PRT
<213> ORGANISM: Homo sapiens
<220> FEATURE:
<221> NAME/KEY: SITE
<222> LOCATION: (1)
<223> OTHER INFORMATION: This site is pyroglutamate.
<221> NAME/KEY: SITE
<222> LOCATION: (3)
<223> OTHER INFORMATION: This site is Tyr or Phe.
<221> NAME/KEY: SITE
<222> LOCATION: (7)
<223> OTHER INFORMATION: This site is Gly, Lys or Pro.
<221> NAME/KEY: SITE
<222> LOCATION: (8)
<223> OTHER INFORMATION: This site is Arg, Cit or Lys.
<221> NAME/KEY: SITE
<222> LOCATION: (9)
<223> OTHER INFORMATION: This site is Arg, Cit or Lys.
<221> NAME/KEY: SITE
<222> LOCATION: (11)
<223> OTHER INFORMATION: This site is Tyr, Phe or Trp.
<221> NAME/KEY: SITE
<222> LOCATION: (1)..(7)
<223> OTHER INFORMATION: Any one of these amino acid residues together
      with those preceding it need not be present.

<400> SEQUENCE: 1

Xaa Leu Xaa Glu Asn Lys Xaa Xaa Xaa Pro Xaa Ile Leu
 1               5                  10

<210> SEQ ID NO 2
<211> LENGTH: 13
<212> TYPE: PRT
<213> ORGANISM: Homo sapiens
<220> FEATURE:
<221> NAME/KEY: SITE
<222> LOCATION: (1)
<223> OTHER INFORMATION: This site is pyroglutamate.

<400> SEQUENCE: 2

Xaa Leu Tyr Glu Asn Lys Pro Arg Arg Pro Tyr Ile Leu
 1               5                  10

<210> SEQ ID NO 3
<211> LENGTH: 6
<212> TYPE: PRT
<213> ORGANISM: Homo sapiens
<220> FEATURE:
<221> NAME/KEY: SITE
<222> LOCATION: (1)
<223> OTHER INFORMATION: This is an acetylated Arg.

<400> SEQUENCE: 3

Xaa Arg Pro Tyr Ile Leu
 1               5

METHOD FOR THE DETECTION AND LOCALIZATION OF DUCTAL EXOCRINE PANCREAS TUMOURS

This application is a 371 PCT/US98/01964, filed Feb. 2, 1998, which claims priority to EP 97200297.6, filed Feb. 3, 1997, both of which are incorporated herein by reference.

The invention relates to a method of detecting and localizing malignant tumours in the body of a human being. The invention further relates to the therapeutic treatment of these tumours in the body of said being. The invention also relates to a pharmaceutical composition to be used in these methods.

Neurotensin (NT) is a neuropeptide that exerts numerous effects in the gastrointestinal tract and in the brain and is already known since a number of years. NT has been studied by several groups, mainly on its normal function in warm-blooded animals and humans. Further it is known in the art that neurotensin receptors are present in several tumour cells, like human colon carcinoma and human meningomas located in or around tissues (colon, brain) which in healthy conditions contain neurotensin receptors (see e.g. WO 95/22341).

Recently radiolabelled octreotide, a cyclic peptide containing 8 amino acid moieties, is commercialized under the brand name OctreoScan® 111. This diagnosticum, labelled with indium-111, is specifically designed for tumour imaging, in particular of tumours in the abdomen (M-D-D-I Reports ("The Gray Sheet") Nov. 2, 1992, p. 14).

It has been observed, however, that various frequently occurring malignant tumours, such as ductal pancreatic adenocarcinomas, cannot be detected and localized by using radiolabelled octreotide.

DETAILED DESCRIPTION OF THE INVENTION

Figure 1:
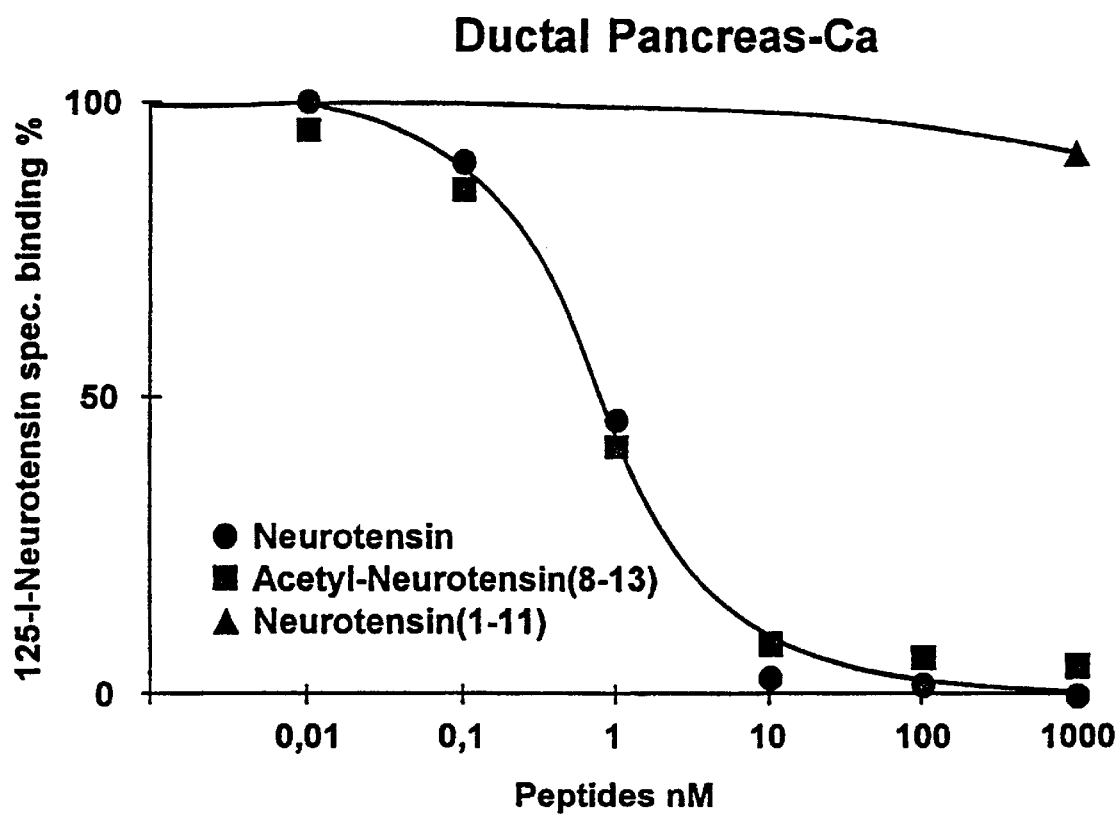
FIG. 1 shows displacement curves of [$^{125}$I]-neurotensin binding to tissue sections from human differentiated ductal pancreatic adenocarcinoma.

It is the objective of the present invention to provide a method of detecting and localizing malignant human tumours and the metastases thereof, in particular the frequently occurring ductal pancreatic tumours, in the body of a human being.

Such a method would be a powerful tool, not only in diagnosing such tumours but also in supporting an effective therapy therefor. As a matter of fact, in order to be able to achieve a specific therapy for the control of such tumours, the detection and localization of these tumours, and in particular of the metastases thereof, in an early stage of their development is of utmost importance. Various requirements have to be imposed on an agent that is used in such a diagnostic method, such as non-toxicity, no adverse influence on the host resistance and/or on the therapeutic treatment, well detectable and highly selective. The required high selectivity means that the diagnostic agent, after having been introduced into the body, must accumulate more strongly in the target tumours to be detected or visualized than in surrounding tissues. This selectivity, i.e. a comparatively stronger concentration of the diagnostic agent in the target tumours compared with non-target tissues, enables the user to correctly diagnose the malignancy. In order to be detectable from outside the body, the diagnostic agent should be labelled, preferably with a radionuclide or with a paramagnetic metal atom. In the former case, the radioactive radiation can be detected by using a suitable detector (scanning). Modern techniques in this field use emission tomography; when gamma radiating isotopes are used, the so-called single photon emission computerized tomography (SPECT) may be applied. The use of paramagnetic diagnostic agents enables a detection by means of imaging by magnetic resonance.

The above defined objective can be achieved, according to the present invention, by method of detecting and localizing malignant tumours and their metastases in tissues, which in healthy condition do not contain substantial quantities of neurotensin-receptors, in the body of a human being, which comprises (i) administering to said being a composition comprising, in a quantity sufficient for external imaging, a peptide selected from the group consisting of neurotensin (NT), NT-receptor agonists, NT-receptor antagonists, NT analogues and NT derivatives, said peptide being labelled with (a) a radioactive metal isotope selected from the group consisting of $^{99m}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52m}$Mn and $^{51}$Cr, or (b) with a paramagnetic metal atom selected from the group consisting Cr, Mn, Fe, Co, Ni, Cu, Pr, Nd, Sm, Yb, Gd, Tb, Dy, Ho and Er, or (c) with a radioactive halogen isotope, selected from $^{123}$I, $^{131}$I, $^{75}$Br, $^{76}$Br, $^{77}$Br and $^{62}$Br, and thereupon (ii) subjecting said being to external imaging, by radioactive scanning or by magnetic resonance imaging, to determine the targeted sites in the body of said being in relation to the background activity, in order to allow detection and localization of said tumours in the body.

The above labelled peptides have been tested in suitable model experiments that are predictive for in vivo application. In these model experiments human tumour tissue samples are used to mimic in vivo application. The experiments are described in the Example appended. From the results it will be evident that the tested labelled peptides have properties which make them pre-eminently suitable for the detection and localization malignant tumours and their metastases in those tissues that in healthy state do not contain substantial amounts of neurotensin receptors.

The present invention is especially useful for the detection and treatment of ductal pancreatic adenocarcinoma. Ductal pancreatic adenocarcinoma is considered to be one of the major lethal cancers. It is usually a rapidly progressive and fatal disease: most patients die within 6 month after diagnosis. Early diagnosis and systemically active therapy is required to improve survival of patients with pancreatic cancer.

In a recent study by Ishizuka et al. (Annals of Surgery 1993, 217, 439–46) it was shown that MIA PaCa-2 human pancreatic cancer cells have neurotensin receptors. According to Yunis et al. (Int. J. Cancer 1977, 19, 128–35), however, these cells are originating from a cell line of an undifferentiated pancreatic carcinoma, which is histologically and biologically not identical with a ductal pancreatic adenocarcinoma. Furthermore it can be concluded from earlier studies of Reubi et al. (Gasteroenterology 1988, 95, 760–3) and Taylor et al. (Peptides 1994, 15, 1229–36) on somatostatin receptors that the expression of receptors in pancreatic tumour cell lines (rat or human) is not predictive at all for their expression in human primary exocrine pancreatic carcinomas. It is therefore a surprising phenomena that the ductal pancreatic adenocarcinoma, in particular the differentiated form, has a high density of neurotensin receptors, while the normal healthy pancreatic tissue does not contain a substantial amount of neurotensin receptors. It is further surprising that neurotensin receptors are not expressed in chronic pancreatitis, which is a presumptive premalignant condition leading to ductal pancreatic carcinomas and which is extremely difficult to differential diagnose from pancreatic carcinomas.

The present invention is also useful for the differential-diagnostic detection of ductal exocrine pancreatic cancers compared to endocrine pancreatic cancers as it has appeared that endocrine pancreatic cancers do not, express neurotensin receptors. Therefore the present invention is a very specific method to detect ductal pancreatic adenocarcinomas, as opposed to endocrine pancreatic cancers or chronic pancreatitis, which would not be visualized.

It is another objective of the present invention to provide a method of intraoperatively detecting and localizing certain malignant human tumours, especially of ductal pancreatic tumours, in the body of a human being.

This objective can be achieved, according to a different aspect of the present invention, by a method of intraoperatively detecting and localizing malignant tumours in tissues, which in healthy condition do not contain substantial quantities of neurotensin-receptors, in the body of a human being, which comprises (i) administering to said being a composition comprising, in a quantity sufficient for detection by a gamma detecting probe, a peptide selected from the group consisting of neurotensin (NT), NT-receptor agonists, NT-receptor antagonists, NT analogues and NT derivatives, said peptide being labelled with $^{161}$Tb, $^{123}$I or $^{125}$I and thereupon (ii), after allowing the active substance to be bound and taken up in said tumours and after blood clearance of radioactivity, subjecting said being to a radioimmunodetection technique in the relevant area of the body of said being, by using a gamma detecting probe.

It is still another objective of the present invention to provide for a method of selective therapeutic treatment without destroying of a substantial part of neighbouring healthy tissue.

This objective can be achieved with a method for the therapeutic treatment of malignant tumours in tissues, which in healthy condition do not contain substantial quantities of neurotensin-receptors, in the body of a human being, which comprises administering to said being a composition comprising, in a quantity effective for combating or controlling tumours, a peptide selected from the group consisting of Neurotensin (NT), NT-receptor agonists, NT-receptor antagonists, NT analogues and NT derivatives, said peptide being labelled with an isotope selected from the group consisting of $^{186}$Re, $^{188}$Re, $^{71}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157\ Gd,}$ $^{159}$Gd, $^{166}$Ho, $^{172}$Tm, $^{169}$Yb, $^{175}$Yb, $^{177}$Lu, $^{105}$Rh, $^{114}$Ag, $^{124}$I and $^{131}$I.

The labelled peptide to be used according to the method of the invention is preferably derived from a compound of the general formula (I)

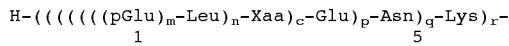
H-(((((((pGlu)$_m$-Leu)$_n$-Xaa)$_c$-Glu)$_p$-Asn)$_q$-Lys)$_r$-
Xbb)$_s$-Xcc-Xdd-Pro-Xee-Ile-Leu-OH (SEQ ID NO:1)

or an acid amide thereof, formed between a free NH$_2$-group of an amino acid moiety and R$_1$COOH, wherein R$_1$ is a (C$_1$–C$_3$)alkanoyl group, an arylcarbonyl group, or an aryl-(C$_1$–C$_3$)alkanoyl group;

or a lactam thereof, formed between a free NH$_2$ group of an amino acid moiety and a free CO$_2$H group of another amino acid moiety;

or a conjugate thereof with avidin or biotin; and wherein:
Xaa is Tyr or Phe;
Xbb is Gly, Lys or Pro;
Xcc is Arg, Cit or Lys;
Xdd is Arg, Cit or Lys;
Xee is Tyr, Phe or Trp;
m, n, o, p, q, r and s each independently are 0 or 1;

Suitable examples of aryl groups in R$_1$ are: phenyl, substituted phenyl or indolyl; preferably phenyl, 4-fluorophenyl, 2- or 4-bromo-phenyl, 2-iodophenyl, 4-hydroxyphenyl, 3-iodo-4-hydroxyphenyl, 4-fluoro-2-bromophenyl and 4-fluoro-2-iodophenyl.

In the case of the use of a conjugate of the peptide with avidin or biotin, the label is attached subsequently by reaction with labelled biotin in the case of avidin-conjugated peptide as described by Kalofonos et al. (J. Nucl. Med. 1990, 31, 1791), or by reaction with labelled avidin in the case of biotin-conjugated peptide as described by Paganelli et al. (Int. J. Cancer 1988, 2, 121).

In the above labelled peptide compounds one or more of the amino acids may have the D-configuration instead of the normal L-configuration.

The labelled peptide compounds of the invention may also comprise so-called pseudo peptide bonds, viz. —CH$_2$—NH— bonds, in addition to the natural amide bonds, viz. —CO—NH— bonds. Such modifications of the amino acids naturally occurring in peptides are within the scope of the present invention. Suitable examples of the above-defined peptides, which after labelling can be used in the method of the invention, are neurotensin and acetylneurotensin 8–13. In formulas:

(1) Neurotensin: H-pGlu-Leu-Tyr-Glu-Asn-Lys-Pro-Arg-Arg-Pro-Tyr-Ile-Leu-OH (SEQ ID NO:2)

(2) Acetylneurotensin 8–13: Ac-Arg-Arg-Pro-Tyr-Ile-Leu-OH (SEQ ID NO:3)

If the peptide as defined above is labelled with a radioactive halogen atom, said radioactive halogen atom is preferably selected from the group consisting of $^{123}$I, $^{124}$I, $^{125}$I, $^{131}$I, $^{75}$Br, $^{76}$Br, $^{77}$Br and $^{92}$Br, said radioactive halogen isotope being attached to a Tyr or Trp moiety of the peptide, or to the aryl group of substituent R$_1$.

The radiohalogenated peptide compounds can be prepared in a manner known per se for related compounds. An example of such a method of preparation is a halogen exchange reaction, wherein a non-radioactive bromine or iodine atom, attached to a Tyrosine residue in the 2-position of the phenyl ring in reacted with a water-soluble radioactive halogenide in the presence of copper(I) ions, a water soluble acid (e.g. citric acid) and a reducing agent(e.g. Sn(II) salts, gentisic acid, isoascorbic acid, a monosaccharide and a sulphite). Such a halogen exchange reaction is described in EP 165630.

If the peptide as defined above is labelled with a metal atom, said metal atom is preferably selected from (a) the group consisting of the radioactive isotopes $^{99m}$Tc, $^{203}$Pb, $^{67}$Ga, $^{66}$Ga, $^{72}$As, $^{111}$In, $^{133m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{195}$Au, $^{199}$Au, $^{161}$Tb, $^{109}$Pd, $^{165}$Dy, $^{149}$Pm, $^{151}$Pm, $^{153}$Sm, $^{157}$Gd, $^{166}$Ho, $^{172}$Tm, $^{169}$Yb, $^{175}$Yb, $^{177}$Lu, $^{105}$Rh and $^{111}$Ag; or (b) the group consisting of the paramagnetic metal ions Cr, Mn, Fe, Co, Ni, Cu, Pr, Nd, Sm, Yb, Gd, Tb, Dy, Ho, and Er; said metal atom being attached to the peptide by means of a chelating group chelating said atom, which chelating group is bound by an amide bond or through a spacing group to the peptide molecule.

Suitable chelating groups for chelating said metal atom are $N_tS_{(4-t)}$ tetradentate chelating agents, wherein t=2–4, or groups derived from ethylene diamine tetra-acetic acid (EDTA), diethylene triamine penta-acetic acid (DTPA), cyclohexyl 1,2-diamine tetra-acetic acid (CDTA), ethyleneglycol-0,0'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N',N'',N'''-tetra-acetic acid (DOTA), hydroxyethyldiamine triacetic acid (HEDTA), 1,4,8,11-tetra-azacyclo-tetradecane-N,N',N'',N'''-tetra-acetic acid (TETA), substituted DTPA, substituted EDTA, or from a compound of the general formula

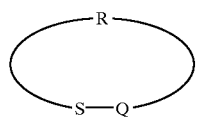

(II)

wherein:
R is a branched or non-branched, optionally substituted hydrocarbyl radical, which may be interrupted by one or more hetero-atoms selected from N, O and S and/or by one or more NH groups, and
Q is a group which is capable of reacting with an amino group of the peptide and which is preferably selected from the group consisting of carbonyl, carbimidoyl, N-($C_1$–$C_6$)alkylcarbimidoyl, N-hydroxycarbimidoyl and N-($C_1$–$C_6$)alkoxycarbimidoyl.

$N_tS_{(4-t)}$ chelating agents, wherein t=2–4, are preferably selected from

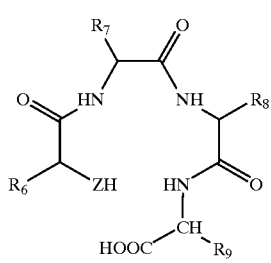

(VI)

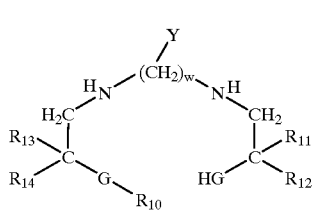

(VII)

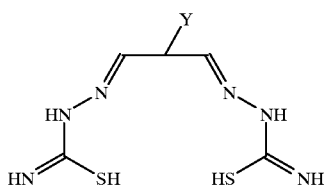

(VIII)

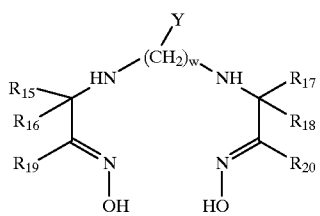

(IX)

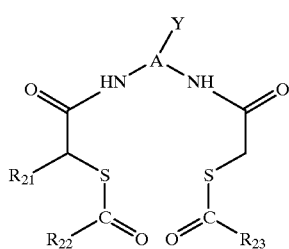

(X)

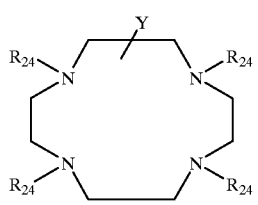

(XI)

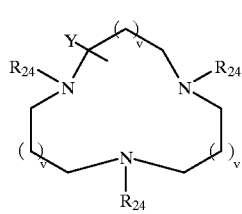

(XII)

wherein:
$R_6$–$R_{20}$ are each individually hydrogen atoms or ($C_1$–$C_4$) alkyl groups, with the proviso that at least one of $C_6$ to $C_9$ is the symbol Y;
$R_{21}$ is a hydrogen atom or a $CO_2(C_1$–$C_4)$alkyl group;
$R_{22}$ and $R_{23}$ are each individually ($C_1$–$C_4$)alkyl groups or phenyl groups;
v is 0 or 1;
w is 2 or 3;
$R_{24}$ is $CH_2COOH$ or a functional derivative thereof;
A is ($C_1$–$C_4$)alkylene, if desired substituted with $CO_2$alkyl, $CH_2CO$alkyl, $CONH_2$, $CONHCH_2CO_2$alkyl; phenylene, phenylene substituted by $CO_2$alkyl, wherein the alkyl groups have 1 to 4 carbon atoms;
G is NH or S;
Y is a functional group capable of binding with a free amino group of the peptide or with the spacing group; and Z is S or O.

Said functional group Y preferably comprises isocyanato, isothiocyanato, formyl, o-halonitrophenyl, diazonium, epoxy, tri-chloro-s-triazinyl, ethyleneimino, chlorosulfonyl, alkoxycarbimidoyl, (substituted or unsubstituted) alkylcarbonyloxycarbonyl, alkyl-carbonylimidazolyl, succinimido-oxycarbonyl; said group being attached to a $(C_1-C_{10})$hydrocarbon biradical.

Suitable examples of hydrocarbon biradicals are biradicals derived from benzene, $(C_1-C_6)$alkanes, $(C_2-C_6)$alkenes and $(C_1-C_4)$-alkylbenzenes.

Examples of suitable chelators of the general formula II are described in the international patent application WO 89/07456, such as unsubstituted or substituted 2-iminothiolanes and 2-iminothia-cyclohexanes, in particular 2-imino-4-mercaptomethylthiolane.

Preferred chelating groups are groups derived from ethylene diamine tetra-acetic acid (EDTA) or 1,4,7,10-tetraazacyclododecane-N,N',N",N'''-tetra-acetic acid (DOTA), as mentioned above.

Suitable examples of spacing groups, if present in the metal-labelled peptide molecule, are groups of the has the general formula

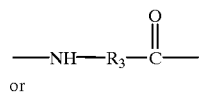

(III)

or

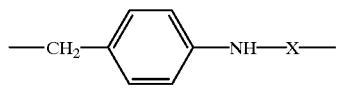

(IV)

wherein $R_3$ is a $C_1-C_{10}$ alkylene group, a $C_1-C_{10}$ alkylidene group or a $C_2-C_{10}$ alkenylene group, and X is a thiocarbonyl group or a group of the general formula

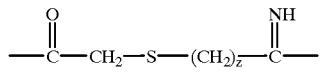

(V)

wherein z is 1–5.

Conjugates with avidin or biotin are formed as described by Paganelli et al. (Int. J. Cancer 1988, 2, 121), Kalofonos et al. (J. Nucl. Med. 1990, 31, 1791) and Anderson et al. (FEBS LETT. 1991, 282/1, 35–40).

The metal-labelled peptides of the invention can be prepared in a manner known per se for related compounds and for some embodiments described in WO 95/22341 and FR 2687680-A1. For this purpose the peptide molecule is derivatized with the desired chelating agent as defined hereinbefore, e.g. $N_tS_{(4-t)}$, EDTA, DTPA, DOTA etc., directly or after introduction of a spacing group as defined above, after which the compound obtained is reacted with a metal isotope, as defined hereinbefore, in the form of a salt or of a chelate bound to a comparatively weak chelator, in order to form a complex.

Suitable examples of salts or chelates of the desired metal atom are: $^{111}$In-oxinate, $^{99m}$Tc-tartrate, etc. The complex-forming reaction can generally be carried out in a simple manner and under conditions that are not detrimental to the peptide.

The invention also relates to the use of a labelled peptide as defined above with the general formula I for the preparation of a diagnostic composition for detecting and localizing or for the therapeutic treatment of malignant human tumours, including the metastases thereof, in tissues, which in healthy condition do not contain substantial quantities of neurotensin receptors, in the body of a human being.

The invention further relates to a pharmaceutical composition to be used for the above-defined method, comprising in addition to a pharmaceutically acceptable carrier material and, if desired, at least one pharmaceutically acceptable adjuvant, as the active substance, in a quantity sufficient for external imaging, for detecting by a gamma detecting probe or for combating or controlling tumours, a labelled peptide as defined in general formula I above, with the proviso that r and s in the formula I are 1.

It is frequently impossible to put the ready-for-use composition at the disposal of the user, in connection with the often poor shelf life of the radiolabelled compound and/or the short half-life of the radionuclide used. In such cases the user will carry out the labelling reaction with the radionuclide in the clinical hospital or laboratory. For this purpose the various reaction ingredients are then offered to the user in the form of a so-called "kit". It will be obvious that the manipulations necessary to perform the desired reaction should be as simple as possible to enable the user to prepare from the kit the radioactive labelled composition by using the facilities that are at his disposal. Therefore the invention also relates to a kit for preparing a radiopharmaceutical composition.

Such a kit according to the present invention for preparing a radiopharmaceutical composition, for detecting and localizing malignant tumours and their metastases in tissues, which in healthy condition do not contain substantial quantities of neurotensin receptors, comprises (i) a derivatized peptide with the general formula (I) as defined above, with the proviso that r and s in the formula (I) are 1, to which derivatized peptide, if desired, an inert pharmaceutically acceptable carrier and/or formulating agents and/or adjuvants is/are added, (ii) a solution of a salt or chelate of a metal isotope selected from the group consisting of $^{203}$Pb, $^{67}$Ga, $^{68}$Ga, $^{72}$As, $^{111}$In, $^{113m}$In, $^{97}$Ru, $^{62}$Cu, $^{99m}$Tc, $^{186}$Re, $^{188}$Re, $^{64}$Cu, $^{52}$Fe, $^{52m}$Mn, $^{51}$Cr, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{166}$Ho, $^{172}$Tm, $^{169}$Yb, $^{175}$Yb, $^{177}$Lu, $^{105}$Rh and $^{111}$Ag, and (iii) instructions for use with a prescription for reacting the ingredients present in the kit.

Preferably the peptide compound to be used as an ingredient of the above kit has been derivatized by a reaction with a chelating agent as defined hereinbefore. The resulting peptide conjugate provides a facility for firmly attaching the radionuclide in a simple manner. Suitable chelating agents for modifying the peptide are described in detail hereinbefore. N-containing di- or polyacetic acids or their derivatives, such as the compounds mentioned before, have proved to be pre-eminently suitable for attaching various metal radionuclides, such as In-111 and In-113m, to the peptide molecules. The kit to be supplied to the user may also comprise the ingredients defined sub (i) above, together with instructions for use, whereas the solution of a salt or chelate of the radionuclide, defined sub (ii) above, which solution has a limited shelf life, may be put to the disposal of the user separately.

In case the kit serves to prepare a radiopharmaceutical composition labelled with Tc-99m, Re-186 or Re-188, such a kit according to the present invention may comprise, in addition to the ingredient(s) defined, sub (i) above, (ii) a reducing agent and, if desired, a chelator, and (iii) instructions for use with a prescription for reacting the ingredients of the kit with Tc-99m in the form of a pertechnetate solution, or with Re-186 or Re-188 in the form of a perrhenate solution. If desired, the ingredients of the kit may be combined, provided they are compatible. The kit should comprise a reducing agent to reduce the pertechnetate or perrhenate, for example, a dithionite, a metallic reducing agent or a complex-stabilizing reducing agent, e.g. $SnCl_2$, Sn(II)-tartrate, Sn(II)-phosphonate or -pyro-phosphate, or Sn(II)-glucoheptonate. The pertechnetate or perrhenate solution can simply be obtained by the user from a suitable generator.

When the radionuclide is present in the kit itself, the complex forming reaction with the derivatized peptide can simply be produced by combining the components in a neutral medium and causing them to react. For that purpose the radionuclide may be presented to the derivatized peptide in the form of a chelate bound to a comparatively weak chelator, as dottribed hereinbefore.

When the kit comprises a derivatized peptide as defined hereinbefore and is intended for the preparation of a radiopharmaceutical composition, labelled with Tc-99m, Re-186 or Re-188, the radionuclide will preferably be added separately in the form of a pertechnetate or perrhenate solution. In that case the kit will comprise a suitable reducing agent and, if desired, a chelator, the former to reduce the pertechnetate or the perrhenate. As a reducing agent may be used, for example, a dithionite or a metallic reducing agent. The ingredients may optionally be combined, provided they are compatible. Such a monocomponent kit, in which the combined ingredients are preferably lyophilized, is excellently suitable for being reacted, by the user, with the radionuclide solution. As a reducing agent for the above-mentioned kits is preferably used a metallic reducing agent, for example, Sn(II), Ce(III), Fe(II), Cu(I), Ti(III) or Sb(III); Sn(II) is excellently suitable. The peptide constituent of the above-mentioned kits, i.e. preferably the derivatized peptide, may be supplied as a solution, for example, in the form of a physiological saline solution, or in some buffer solution, but is preferably present in a dry condition, for example, in the lyophilized condition. When used as a component for an injection liquid it should be sterile, in which, when the constituent is in the dry state, the user should preferably use a sterile physiological saline solution as a solvent. If desired, the above-mentioned constituent may be stabilized in the conventional manner with suitable stabilizers, for example, ascorbic acid, gentisic acid or salts of these acids, or it may comprise other auxiliary agents, for example, fillers, such as glucose, lactose, mannitol, and the like.

The invention will now be described in greater detail with reference to the following specific Example.

EXAMPLE 1

Receptor autoradiography is performed on 10- and 20-mm thick cryostat sections of the various tumour samples, as described by Reubi et al. (Cancer Res. 1990, 50, 5969–5977).

Unlabelled neurotensin, neurotensin 1–11 and acetyl neurotosin 8–13 are obtained from Bachem AG, Bubendorf, Switzerland.

$^{125}$I-labelled peptides are prepared via the chloramine T iodination procedure, according to procedures as reported earlier by Greenwood et al. (Biochemical Journal 1963, 89, 114–123).

The $^{125}$I labelled neurotensin is separated by HPLC, using a reverse phase $RC_{18}$ column and butane-sulphonic acid as the eluent. The mono-$^{125}$ iodinated compound (pGlu-Leu-$^{125}$I-Tyr-Glu-Asn-Lys-Pro-Arg-Arg-Pro-Tyr-Ile-Leu) is eluted as single peak from the HPLC and analysed by mass-spectrometry. Specific activity: 2000 Ci/mmol. The tissues are cut on a cryostat, mounted on microscope slides, and then stored at −20° C. for at least 3 days to improve adhesion of the tissue to the slide. The slide-mounted tissue sections ac allowed to reach room temperature. The slides are then incubated in a solution of 40,000 dpm/100 $\mu$l monoiodo [$^{125}$I]Tyr$^3$-neurotensin (2000 Ci/mmole) in 50 mM Tris-HCl buffer, pH 7.6, containing 5 mM $MgCl_2$, 0.2% bovine serum albumin and $5*10^{-5}$ M bacitracin at 4° C. for 60 minutes. Additional sections are incubated in the presence of 0.5 $\mu$M native neurotensin for determination of non-specific binding. After incubation, the sections are washed for eight minutes at 4° C. in four consecutive baths containing 50 mM Tris-HCl buffer, pH 7.6, dipped in ice-cold water, and then quickly dried in a refrigerator under a stream of cold air. The sections are subsequently exposed to a $^3$H-Ultrofilm for 1 week, to detect the precise location of the radioactivity.

Displacement experiments using successive sections of a tumour are performed with increasing concentrations of various biologically active or inactive peptides (see the above-mentioned publication by Reubi et al.). In comparison with neurotensin, neurotensin 1–11 and acetyl neurotensin 8–13 are used.

The FIG. 1 attached shows displacement curves of [$^{125}$I]-neurotensin binding to tissue sections from human differentiated ductal pancreatic adenocarcinoma. Tissue sections are incubated with 40,000 cpm/100 $\mu$l [$^{125}$I]-neurotensin and increasing concentrations of unlabeled neurotensin, neurotensin 1–11 or acetylneurotensin 8–13. Each point represents the optical density of binding measured in the tumour area. Non-specific binding is subtracted from all values. Complete displacement of the ligand is achieved by neurotensin or acetyl-neurotensin 8–13, whereas neurotensin 1–11 is inactive in the nanomolar range.

This experiment shows that ductal pancreatic adenocarcinomas have neurotensin receptors with high affinity for biologically active neurotensin analogs only.

EXAMPLE 2

Receptor autoradiography on various human pancreatic tissues is performed as described in Example 1 with the aid of $^{125}$I labelled neurotensin. The neurotensin receptor density is measured by a computer assisted image processing system as described by Reubi et al. (Cancer Res. 1990, 50, 5969–5977), using tissue standards for iodinated compounds from Amersham. The receptor density is expressed in desintegrations per minute (dpm)/mg tissue.

Figure 2:
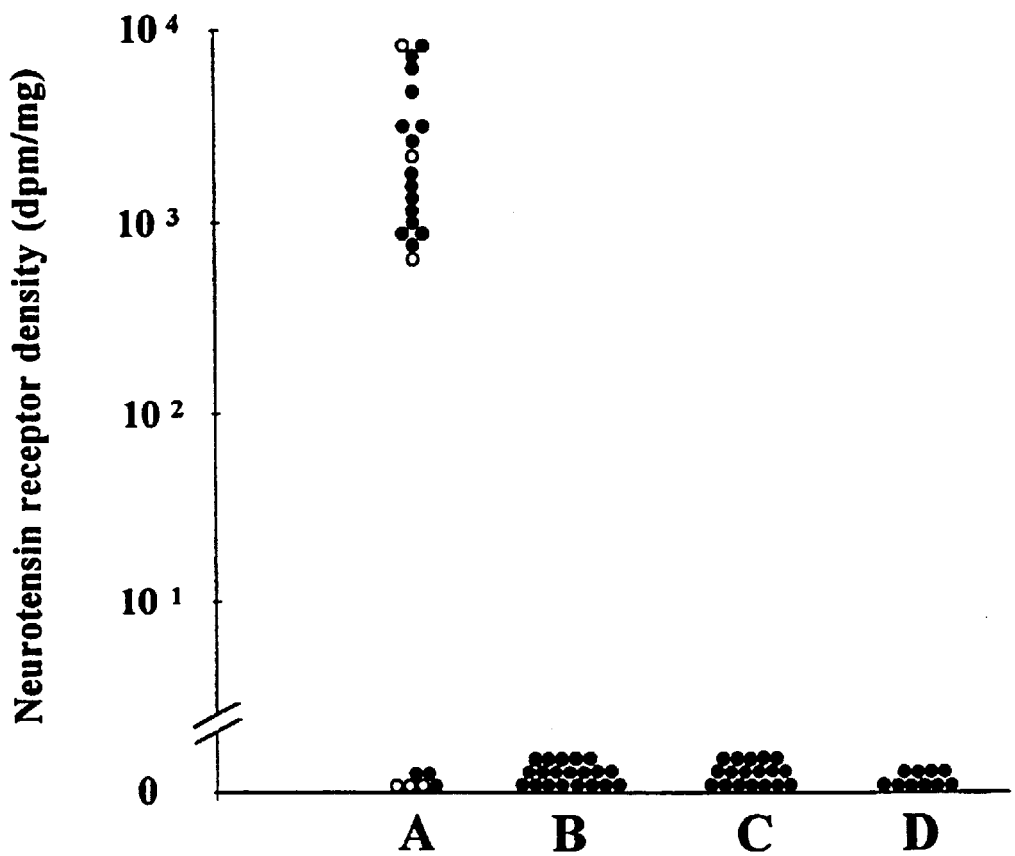
FIG. 2 shows the density of neurotensin receptors on: (A) ductal pancreatic adenocarcinomas—(●) differentiated tumours of grade I or II and (○) poorly differentiated tumours of grade II–III or III, (B) endocrine pancreatic cancer, (C) chronic pancreatitis, and (D) normal pancreas.

FIG. 2 attached shows the density of neurotensin receptors on:
  A: Ductal pancreatic adenocarcinomas (n=24), 18 cases are differentiated (●) tumours (grade I or II), 6 cases are poorly differentiated (○) tumours (grade II–III or III).
  B. Endocrine pancreatic cancers (n=20)
  C. Chronic pancreatitis (n=18)
  D. Normal pancreas (N=10)

This example illustrates that neurotensin receptors are expressed in 75% of human pancreatic carcinomas (A), whereas they are completely absent in normal human pancreas (D), chronic pancreatitis (C) and in endocrine pancreatic cancers (B). Further it appears that differentiated tumours (grade I or II) are more often neurotensin receptor-positive than poorly differentiated tumours (grade II–III and III).

What is claimed is:

1. A method of detecting and localizing Ductal Exocrine Pancreas tumours and their metastases in tissues, which in healthy condition and in non-neoplastic conditions of chronic inflammation do not contain substantial quantities of neurotensin-receptors, in the body of a human being, which comprises (i) administering to said being a composition comprising, in a quantity sufficient for external imaging, a peptide selected from the group consisting of neurotensin (NT), NT-receptor agonists, NT-receptor antagonists, NT analogues and NT derivatives, said peptide being labelled with (a) a radioactive metal isotope selected from the group consisting of $^{99m}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52m}$Mn and $^{51}$Cr, or (b) with a paramagnetic metal atom selected from the group consisting of Cr, Mn, Fe, Co, Ni, Cu, Pr, Nd, Sm, Yb, Gd, Tb, Dy, Ho and Er, or (c) with a radioactive halogen isotope, selected from $^{123}$I, $^{124}$I, $^{125}$I, $^{131}$I, $^{75}$Br, $^{76}$Br, $^{77}$Br and $^{82}$Br, and thereupon (ii) subjecting said being to external imaging, by radioactive scanning or by magnetic resonance imaging, to determine the targeted sites in the body of said being in relation to the background activity, in order to allow detection and localization of said tumours in the body.

2. A method of intraoperatively detecting and localizing Ductal Exocrine Pancreas tumours in tissues, which in healthy condition and in non-neoplastic conditions of chronic inflammation do not contain substantial quantities of neurotensin-receptors, in the body of a human being, which comprises (i) administering to said being a composition comprising, in a quantity sufficient for detection by a gamma detecting probe, a peptide selected from the group consisting of neurotensin (NT), NT-receptor agonists, NT-receptor antagonists, NT analogues and NT derivatives, said peptide being labelled with $^{161}$Tb, $^{123}$I or $^{125}$I and thereupon (ii), after allowing the active substance to be bound and taken up in said tumours and after blood clearance of radioactivity, subjecting said being to a radioimmunodetection technique in the relevant area of the body of said being, by using a gamma detecting probe.

3. A method for the therapeutic treatment of Ductal Exocrine Pancreas tumours in tissues, which in healthy condition and in non-neoplastic conditions of chronic inflammation do not contain substantial quantities of neurotensin-receptors, in the body of a human being, which comprises administering to said being a composition comprising, in a quantity effective for combating or controlling tumours, a peptide selected from the group consisting of Neurotensin (NT), NT-receptor agonists, NT-receptor antagonists, NT analogues and NT derivatives, said peptide being labelled with an isotope selected from the group consisting of $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{111}$Ag, $^{124}$I and $^{131}$I.

4. The method of claim 1, 2 or 3, wherein the Ductal Exocrine Pancreas tumours are present in Pancreatic tissue.

5. The method of claim 1 or 2, wherein said Ductal Exocrine Pancreas tumours are detected differentially from Endocrine Pancreatic Carcinoma.

6. The method of claim 1 or 2, which comprises administering to said living being a composition comprising a labelled peptide, derived from a compound of the general formula

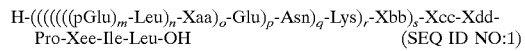

H-(((((((pGlu)$_m$-Leu)$_n$-Xaa)$_o$-Glu)$_p$-Asn)$_q$-Lys)$_r$-Xbb)$_s$-Xcc-Xdd-Pro-Zee-Ile-Leu-OH   (SEQ ID NO:1)

or an acid amide thereof, formed between a free $NH_2$-group of an amino acid moiety and $R_1COOH$, wherein:

$R_1$ is a $(C_1–C_3)$alkanoyl group, an arylcarbonyl group, or an aryl-$(C_1–C_3)$alkanoyl group; or a lactam thereof, formed between a free $NH_2$ group of an amino acid moiety and a free $CO_2H$ group of another amino acid moiety;

or a conjugate thereof with avidin or biotin; and wherein:

Xaa is Tyr or Phe;

Xbb is Gly, Lys or Pro;

Xcc is Arg, Cit or Lys;

Xdd is Arg, Cit or Lys;

Xee is Tyr, Phe or Trp;

m, n, o, p, q, r and s each independently are 0 or 1.

7. The method of claim 3, which comprises administering to said living being a composition comprising a labelled peptide, derived from a compound of the general formula

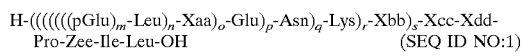

H-(((((((pGlu)$_m$-Leu)$_n$-Xaa)$_o$-Glu)$_p$-Asn)$_q$-Lys)$_r$-Xbb)$_s$-Xcc-Xdd-Pro-Xee-Ile-Leu-OH   (SEQ ID NO:1)

or an acid amide thereof, formed between a free $NH_2$-group of an amino acid moiety and $R_1COOH$, wherein:

$R_1$ is a $(C_1–C_3)$alkanoyl group, an arylcarbonyl group, or an aryl-$(C_1–C_3)$alkanoyl group; or a lactam thereof, formed between a free $NH_2$ group of an amino acid moiety and a free $CO_2H$ group of another amino acid moiety;

or a conjugate thereof with avidin or biotin; and wherein:

Xaa is Tyr or Phe;

Xbb is Gly, Lys or Pro;

Xcc is Arg, Cit or Lys;

Xdd is Arg, Cit or Lys;

Xee is Tyr, Phe or Trp;

m, n, o, p, q, r and s each independently are 0 or 1.

8. The method of claim 6 wherein said Ductal Exocrine Pancreas tumours are present in pancreatic tissue.

9. The method of claim 7 wherein said Ductal Exocrine Pancreas tumours are present in pancreatic tissue.

10. The method of claim 8 wherein said Ductal Exocrine Pancreas tumours are detected differentially from endocrine pancreatic carcinoma.

11. The method of claim 1 or 2, which comprises administering to said living being a composition comprising a labelled peptide as defined in said claims, wherein said peptide is labelled with a radioactive halogen isotope selected from the group consisting of $^{123}$I, $^{124}$I, $^{125}$I, $^{131}$I, $^{75}$Br, $^{76}$Br, $^{77}$Br and $^{82}$Br, said radioactive halogen isotope being attached to a Tyr or Trp moiety of the peptide, or to the aryl group of substituent $R_1$.

12. The method of claim 3, which comprises administering to said living being a composition comprising a labelled peptide as defined in said claims, wherein said peptide is labelled with a radioactive halogen isotope selected from the group consisting of $^{123}$I, $^{124}$I, $^{125}$I, $^{131}$I, $^{75}$Br, $^{76}$Br, $^{77}$Br and $^{82}$Br, said radioactive halogen isotope being attached to a Tyr or Trp moiety of the peptide, or to the aryl group of substituent $R_1$.

13. The method of claim 11 wherein said Ductal Exocrine Pancreas tumours are present in pancreatic tissue.

14. The method of claim 12 wherein said Ductal Exocrine Pancreas tumours are present in pancreatic tissue.

15. The method of claim 13 wherein said Ductal Exocrine Pancreas tumours are detected differentially from endocrine pancreatic carcinoma.

16. The method of claim 6 wherein said peptide is labelled with a radioactive halogen isotope selected from the group consisting of $^{123}$I, $^{124}$I, $^{125}$I, $^{131}$I, $^{75}$Br, $^{76}$Br, $^{77}$Br and $^{82}$Br, said radioactive halogen isotope being attached to a Tyr or Trp moiety of the peptide, or to the aryl group of substituent $R_1$.

17. The method of claim 7 wherein said peptide is labelled with a radioactive halogen isotope selected from the group consisting of $^{123}$I, $^{124}$I, $^{125}$I, $^{131}$I, $^{75}$Br, $^{76}$Br, $^{77}$Br, and $^{82}$Br, said radioactive halogen isotope being attached to a Tyr or Trp moiety of the peptide, or to the aryl group of substituent $R_1$.

18. The method of claim 1 or 2, which comprises administering to said living being a composition comprising a labelled peptide as defined in said claims, wherein said peptide is labelled with a metal atom selected from (a) the group consisting of the radioactive isotopes $^{99m}$Tc, $^{203}$Pb, $^{66}$Ga, 67Ga, $^{68}$Ga, $^{72}$As, $^{111}$In, $^{113m}$In, $^{114m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{117m}$Sn, $^{121}$Sn, $^{127}$Te, $^{142}$Pr, $^{143}$Pr, $^{198}$Au, $^{199}$Au, $^{149}$Tb, $^{161}$Tb, $^{109}$Pd, $^{165}$Dy, $^{149}$Pm, $^{151}$Pm, $^{153}$Sm, $^{157}$Gd, $^{166}$Ho, $^{172}$Tm, $^{169}$Yb, $^{175}$Yb, $^{177}$Lu, $^{105}$Rh, and $^{111}$Ag or (b) the group consisting of the paramagnetic metal atoms Cr, Mn, Fe, Co, Ni, Cu, Pr, Nd, Sm, Yb, Gd, Tb, Dy, Ho and Er; said metal atom being attached to the peptide by means of a chelating group chelating said atom, which chelating group is bound by an amide bond or through a spacing group to the peptide molecule.

19. The method of claim 3, which comprises administering to said living being a composition comprising a labelled peptide as defined in said claims, wherein said peptide is labelled with a metal atom selected from (a) the group consisting of the radioactive isotopes $^{99m}$Tc, $^{203}$Pb, $^{66}$Ga, $^{67}$Ga, $^{68}$Ga, $^{72}$As, $^{111}$In, $^{113m}$In, $^{114m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{117m}$Sn, $^{121}$Sn, $^{127}$Te, $^{142}$Pr, $^{143}$Pr, $^{198}$Au, $^{199}$Au, $^{149}$Tb, $^{161}$Tb, $^{109}$Pd, $^{165}$Dy, $^{149}$Pm, $^{151}$Pm, $^{153}$Sm, $^{157}$Gd, $^{166}$Ho, $^{172}$Tm, $^{169}$Yb, $^{175}$Yb, $^{177}$Lu, $^{105}$Rh, and $^{111}$Ag or (b) the group consisting of the paramagnetic metal atoms Cr, Mn, Fe, Co, Ni, Cu, Pr, Nd, Sm, Yb, Gd, Tb, Dy, Ho and Er; said metal atom being attached to the peptide by means of a chelating group chelating said atom, which chelating group is bound by an amide bond or through a spacing group to the peptide molecule.

20. The method of claim 18 wherein said Ductal Exocrine Pancreatic tumours are present in pancreatic tissue.

21. The method of claim 19 wherein said Ductal Exocrine Pancreatic tumours are present in pancreatic tissue.

22. The method of claim 20 wherein said Ductal Exocrine Pancreas tumors are detected differentially from endocrine pancreatic carcinoma.

23. The method of claim 6 wherein said peptide is labelled with a metal atom selected from (a) the group consisting of the radioactive isotopes $^{99m}$Tc, $^{203}$Pb, $^{66}$Ga, $^{67}$Ga, $^{68}$Ga, $^{72}$As, $^{111}$In, $^{113m}$In, $^{114m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{117m}$Sn, $^{121}$Sn, $^{127}$Te, $^{142}$Pr, $^{143}$Pr, $^{198}$Au, $^{199}$Au, $^{149}$Tb, $^{161}$Tb, $^{109}$Pd, $^{165}$Dy, $^{149}$Pm, $^{151}$Pm, $^{153}$Sm, $^{157}$Gd, $^{166}$Ho, $^{172}$Tm, $^{169}$Yb, $^{175}$Yb, $^{177}$Lu, $^{105}$Rh, and $^{111}$Ag or (b) the group consisting of the paramagnetic metal atoms Cr, Mn, Fe, Co, Ni, Cu, Pr, Nd, Sm, Yb, Gd, Tb, Dy, Ho and Er; said metal atom being attached to the peptide by means of a chelating group chelating said atom, which chelating group is bound by an amide bond or through a spacing group to the peptide molecule.

24. The method of claim 7 wherein said peptide is labelled with a metal atom selected from (a) the group consisting of the radioactive isotopes $^{99m}$Tc, $^{203}$Pb, $^{66}$Ga, $^{67}$Ga, $^{68}$Ga, $^{72}$As, $^{111}$In, $^{113m}$In, $^{114m}$In, $^{97}$Ru, $^{62}$Cu, $^{64}$Cu, $^{52}$Fe, $^{52m}$Mn, $^{52}$Cr, $^{186}$Re, $^{188}$Re, $^{77}$As, $^{90}$Y, $^{67}$Cu, $^{169}$Er, $^{117m}$Sn, $^{121}$Sn, $^{127}$Te, $^{142}$Pr, $^{143}$Pr, $^{198}$Au, $^{199}$Au, $^{149}$Tb, 161Tb, $^{109}$Pd, $^{165}$Dy, $^{149}$Pm, $^{151}$Pm, $^{153}$Sm, $^{157}$Gd, $^{166}$Ho, $^{172}$Tm, $^{169}$Yb, $^{175}$Yb, $^{177}$Lu, $^{105}$Rh, and $^{111}$Ag or (b) the group consisting of the paramagnetic metal atoms Cr, Mn, Fe, Co, Ni, Cu, Pr, Nd, Sm, Yb, Gd, Tb, Dy, Ho and Er; said metal atom being attached to the peptide by means of a chelating group chelating said atom, which chelating group is bound by an amide bond or through a spacing group to the peptide molecule.

25. The method of claim 11 wherein said peptide is labelled with a metal atom selected from (a) the group consisting of the radioactive isotopes $^{99m}$Tc, $^{203}$Pb, $^{66}$Ga, $^{67}$Ga, $^{68}$Ga, $^{72}$As, $^{111}$In, $^{113m}$In, $^{114m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{117m}$Sn, $^{121}$Sn, $^{127}$Te, $^{142}$Pr, $^{143}$Pr, $^{198}$Au, $^{199}$Au, $^{149}$Tb, $^{161}$Tb, $^{109}$Pd, $^{165}$Dy, $^{149}$Pm, $^{151}$Pm, $^{153}$Sm, $^{157}$Gd, $^{166}$Ho, $^{172}$Tm, $^{169}$Yb, $^{175}$Yb, $^{177}$Lu, $^{105}$Rh, and $^{111}$Ag or (b) the group consisting of the paramagnetic metal atoms Cr, Mn, Fe, Co, Ni, Cu, Pr, Nd, Sm, Yb, Gd, Tb, Dy, Ho and Er; said metal atom being attached to the peptide by means of a chelating group chelating said atom, which chelating group is bound by an amide bond or through a spacing group to the peptide molecule.

26. The method of claim 12 wherein said peptide is labelled with a metal atom selected from (a) the group consisting of the radioactive isotopes $^{99m}$Tc, $^{203}$Pb, $^{66}$Ga, $^{67}$Ga, $^{68}$Ga, $^{72}$As, $^{111}$In, $^{113m}$In, $^{114m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{117m}$Sn, $^{121}$Sn, $^{127}$Te, $^{142}$Pr, $^{143}$Pr, $^{198}$Au, $^{199}$Au, $^{149}$Tb, $^{161}$Tb, $^{109}$Pd, $^{165}$Dy, $^{149}$Pm, $^{151}$Pm, $^{153}$Sm, $^{157}$Gd, $^{166}$Ho, $^{172}$Tm, $^{169}$Yb, $^{175}$Yb, $^{177}$Lu, $^{105}$Rh, and $^{111}$Ag or (b) the group consisting of the paramagnetic metal atoms Cr, Mn, Fe, Co, Ni, Cu, Pr, Nd, Sm, Yb, Gd, Tb, Dy, Ho and Er; said metal atom being attached to the peptide by means of a chelating group chelating said atom, which chelating group is bound by an amide bond or through a spacing group to the peptide molecule.

27. The method of claim 18, wherein said composition comprises a peptide labelled with a metal atom, chelated by an $N_tS_{(4-t)}$ tetradentate chelating agent, wherein t=2–4, or by a chelating group derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N',N",N'''-tetra-acetic acid (DOTA), hydroxyethyldiamine triacetic acid (HEDTA), 1,4,8,11-tetraazacyclotetradecane-N,N',N",N'''-tetra-acetic acid (TETA), substituted DTPA, substituted EDTA, or from a compound of the general formula (II)

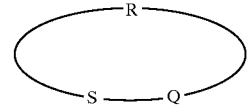

wherein:

R is a branched or non-branched, optionally substituted hydrocarbyl radical, which may be interrupted by one or more hetero-atoms selected from N, O and S and/or by one or more NH groups, and Q is selected from the group consisting of carbonyl, carbimidoyl, N-($C_1$-$C_6$)alkylcarbimidoyl, N-hydroxycarbimidoyl and N-($C_1$-$C_6$)alkoxycarbimidoyl; and wherein said peptide optionally comprises a spacing group wherein said spacing group is a biotinyl moiety or has the general formula (III)

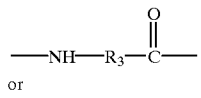

or

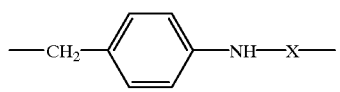 (IV)

wherein $R_3$ is a $C_1$–$C_{10}$ alkylene group, a $C_1$–$C_{10}$ alkylidene group or a $C_2$–$C_{10}$ alkenylene group, and X is a thiocarbonyl group or a group of the general formula

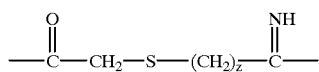 (V)

wherein z is 1–5.

28. The method of claim 19, wherein said composition comprises a peptide labelled with a metal atom, chelated by an $N_tS_{(4-t)}$ tetradentate chelating agent, wherein t=2–4, or by a chelating group derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N',N'',N'''-tetra-acetic acid (DOTA), hydroxyethyldiamine triacetic acid (HEDTA), 1,4,8,11-tetraazacyclotetradecane-N,N',N'',N'''-tetra-acetic acid (TETA), substituted DTPA, substituted EDTA, or from a compound of the general formula

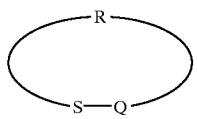 (II)

wherein:
R is a branched or non-branched, optionally substituted hydrocarbyl radical, which may be interrupted by one or more hetero-atoms selected from N, O and S and/or by one or more NH groups, and
Q is selected from the group consisting of carbonyl, carbimidoyl, N-($C_1$–$C_6$)alkylcarbimidoyl, N-hydroxycarbimidoyl and N-($C_1$–$C_6$)alkoxycarbimidoyl; and
wherein said peptide optionally comprises a spacing group wherein said spacing group is a biotinyl moiety or has the general formula

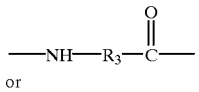 (III)

or

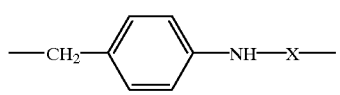 (IV)

wherein $R_3$ is a $C_1$–$C_{10}$ alkylene group, a $C_1$–$C_{10}$ alkylidene group or a $C_2$–$C_{10}$ alkenylene group, and X is a thiocarbonyl group or a group of the general formula

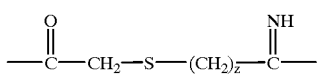 (V)

wherein z is 1–5.

29. The method of claim 20, wherein said composition comprises a peptide labelled with a metal atom, chelated by an $N_tS_{(4-t)}$ tetradentate chelating agent, wherein t=2–4, or by a chelating group derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N',N'',N'''-tetra-acetic acid (DOTA), hydroxyethyldiamine triacetic acid (HEDTA), 1,4,8,11-tetraazacyclotetradecane-N,N',N'',N'''-tetra-acetic acid (TETA), substituted DTPA, substituted EDTA, or from a compound of the general formula

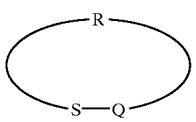 (II)

wherein:
R is a branched or non-branched, optionally substituted hydrocarbyl radical, which may be interrupted by one or more hetero-atoms selected from N, O and S and/or by one or more NH groups, and
Q is selected from the group consisting of carbonyl, carbimidoyl, N-($C_1$–$C_6$)alkylcarbimidoyl, N-hydroxycarbimidoyl and N-($C_1$–$C_6$)alkoxycarbimidoyl; and
wherein said peptide optionally comprises a spacing group wherein said spacing group is a biotinyl moiety or has the general formula

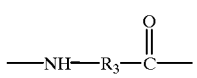 (III)

or

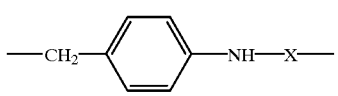 (IV)

wherein $R_3$ is a $C_1$–$C_{10}$ alkylene group, a $C_1$–$C_{10}$ alkylidene group or a $C_2$–$C_{10}$ alkenylene group, and X is a thiocarbonyl group or a group of the general formula

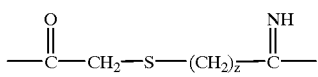 (V)

wherein z is 1–5.

30. The method of claim 21, wherein said composition comprises a peptide labelled with a metal atom, chelated by an N$_t$S$_{(4-t)}$ tetradentate chelating agent, wherein t=2–4, or by a chelating group derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N',N'',N'''-tetra acetic acid (DOTA), hydroxyethyldiamine triacetic acid (HEDTA), 1,4,8,11-tetraazacyclotetradecane-N,N',N'',N'''-tetra-acetic acid (TETA), substituted DTPA, substituted EDTA, or from a compound of the general formula

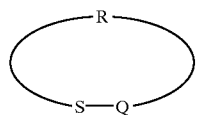

(II)

wherein:

R is a branched or non-branched, optionally substituted hydrocarbyl radical, which may be interrupted by one or more hetero-atoms selected from N, O and S and/or by one or more NH groups, and Q is selected from the group consisting of carbonyl, carbimidoyl, N-(C$_1$–C$_6$)alkylcarbimidoyl, N-hydroxycarbimidoyl and N-(C$_1$–C$_6$)alkoxycarbimidoyl; and wherein said peptide optionally comprises a spacing group wherein said spacing group is a biotinyl moiety or has the general formula

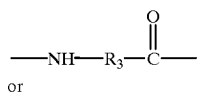

(III)

or

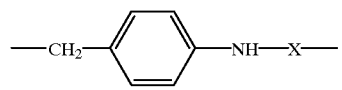

(IV)

wherein R$_3$ is a C$_1$–C$_{10}$ alkylene group, a C$_1$–C$_{10}$ alkylidene group or a C$_2$–C$_{10}$ alkenylene group, and X is a thiocarbonyl group or a group of the general formula

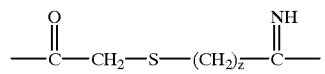

(V)

wherein z is 1–5.

31. The method of claim 22, wherein said composition comprises a peptide labelled with a metal atom, chelated by an N$_t$S$_{(4-t)}$ tetradentate chelating agent, wherein t=2–4, or by a chelating group derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N',N'',N'''-tetra-acetic acid (DOTA), hydroxyethyldiamine triacetic acid (HEDTA), 1,4,8,11-tetraazacyclotetradecane-N,N',N'',N'''-tetra-acetic acid (TETA), substituted DTPA, substituted EDTA, or from a compound of the general formula

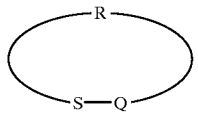

(II)

wherein:

R is a branched or non-branched, optionally substituted hydrocarbyl radical, which may be interrupted by one or more hetero-atoms selected from N, O and S and/or by one or more NH groups, and Q is selected from the group consisting of carbonyl, carbimidoyl, N-(C$_1$–C$_6$)alkylcarbimidoyl, N-hydroxycarbimidoyl and N-(C$_1$–C$_6$)alkoxycarbimidoyl; and wherein said peptide optionally comprises a spacing group wherein said spacing group is a biotinyl moiety or has the general formula

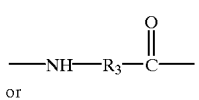

(III)

or

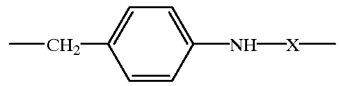

(IV)

wherein R$_3$ is a C$_1$–C$_{10}$ alkylene group, a C$_1$–C$_{10}$ alkylidene group or a C$_2$–C$_{10}$ alkenylene group, and X is a thiocarbonyl group or a group of the general formula

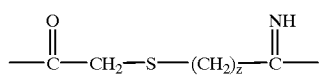

(V)

wherein z is 1–5.

32. The method of claim 23, wherein said composition comprises a peptide labelled with a metal atom, chelated by an N$_t$S$_{(4-1)}$ tetradentate chelating agent, wherein t=2–4, or by a chelating group derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N',N'',N'''-tetra-acetic acid (DOTA), hydroxyethyldiamine triacetic acid (HEDTA), 1,4,8,11-tetraazacyclotetradecane-N,N',N'',N'''-tetra-acetic acid (TETA), substituted DTPA, substituted EDTA, or from a compound of the general formula

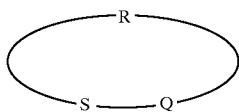 (II)

wherein:

R is a branched or non-branched, optionally substituted hydrocarbyl radical, which may be interrupted by one or more hetero-atoms selected from N, O and S and/or by one or more NH groups, and Q is selected from the group consisting of carbonyl, carbimidoyl, N-($C_1$-$C_6$)alkylcarbimidoyl, N-hydroxycarbimidoyl and N-($C_1$-$C_6$)alkoxycarbimidoyl; and wherein said peptide optionally comprises a spacing group wherein said spacing group is a biotinyl moiety or has the general formula

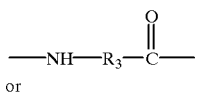 (III)

or

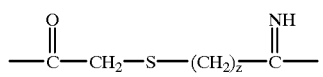 (IV)

wherein $R_3$ is a $C_1$-$C_{10}$ alkylene group, a $C_1$-$C_{10}$ alkylidene group or a $C_2$-$C_{10}$ alkenylene group, and X is a thiocarbonyl group or a group of the general formula

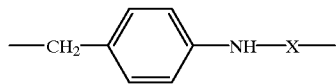 (V)

wherein z is 1–5.

33. The method of claim 24, wherein said composition comprises a peptide labelled with a metal atom, chelated by an $N_tS_{(4-t)}$ tetradentate chelating agent, wherein t=2–4, or by a chelating group derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N',N'',N'''-tetra-acetic acid (DOTA), hydroxyethyldiamine triacetic acid (HEDTA), 1,4,8,11-tetraazacyclotetradecane-N,N',N'',N'''-tetra-acetic acid (TETA), substituted DTPA, substituted EDTA, or from a compound of the general formula

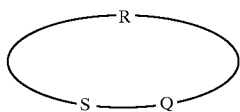 (II)

wherein:

R is a branched or non-branched, optionally substituted hydrocarbyl radical, which may be interrupted by one or more hetero-atoms selected from N, O and S and/or by one or more NH groups, and Q is selected from the group consisting of carbonyl, carbimidoyl, N-($C_1$-$C_6$)alkylcarbimidoyl, N-hydroxycarbimidoyl and N-($C_1$-$C_6$)alkoxycarbimidoyl; and wherein said peptide optionally comprises a spacing group wherein said spacing group is a biotinyl moiety or has the general formula

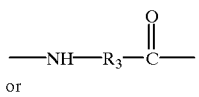 (III)

or

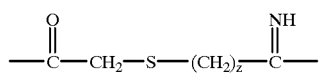 (IV)

wherein $R_3$ is a $C_1$-$C_{10}$ alkylene group, a $C_1$-$C_{10}$ alkylidene group or a $C_2$-$C_{10}$ alkenylene group, and X is a thiocarbonyl group or a group of the general formula

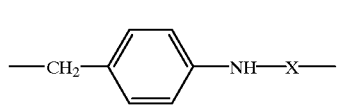 (V)

wherein z is 1–5.

34. The method of claim 25, wherein said composition comprises a peptide labelled with a metal atom, chelated by an $N_tS_{(4-t)}$ tetradentate chelating agent, wherein t=2–4, or by a chelating group derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N',N'',N'''-tetra-acetic acid (DOTA), hydroxyethyldiamine triacetic acid (HEDTA), 1,4,8,11-tetraazacyclotetradecane-N,N',N'',N'''-tetra-acetic acid (TETA), substituted DTPA, substituted EDTA, or from a compound of the general formula

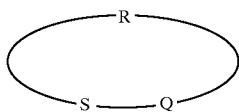
(II)

wherein:
R is a branched or non-branched, optionally substituted hydrocarbyl radical, which may be interrupted by one or more hetero-atoms selected from N, O and S and/or by one or more NH groups, and Q is selected from the group consisting of carbonyl, carbimidoyl, N-($C_1$-$C_6$)alkylcarbimidoyl, N-hydroxycarbimidoyl and N-($C_1$-$C_6$)alkoxycarbimidoyl; and wherein said peptide optionally comprises a spacing group wherein said spacing group is a biotinyl moiety or has the general formula

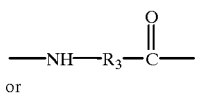
(III)

or

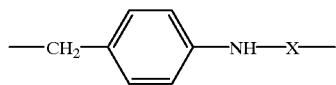
(IV)

wherein $R_3$ is a $C_1$–$C_{10}$ alkylene group, a $C_1$–$C_{10}$ alkylidene group or a $C_2$–$C_{10}$ alkenylene group, and X is a thiocarbonyl group or a group of the general formula

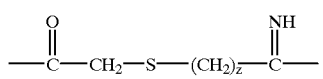
(V)

wherein z is 1–5.

35. The method of claim 26, wherein said composition comprises a peptide labelled with a metal atom, chelated by an $N_tS_{(4-t)}$ tetradentate chelating agent, wherein t=2–4, or by a chelating group derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N',N'',N'''-tetra-acetic acid (DOTA), hydroxyethyldiamine triacetic acid (HEDTA), 1,4,8,11-tetraazacyclotetradecane-N,N',N'',N'''-tetra-acetic acid (TETA), substituted DTPA, substituted EDTA, or from a compound of the general formula

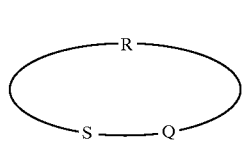
(II)

wherein
R is a branched or non-branched, optionally substituted hydrocarbyl radical, which may be interrupted by one or more hetero-atoms selected from N, O and S and/or by one or more NH groups, and Q is selected from the group consisting of carbonyl, carbimidoyl, N-($C_1$-$C_6$)alkylcarbimidoyl, N-hydroxycarbimidoyl and N-($C_1$-$C_6$)alkoxycarbimidoyl; and wherein said peptide optionally comprises a spacing group wherein said spacing group is a biotinyl moiety or has the general formula

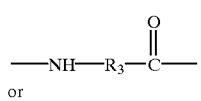
(III)

or

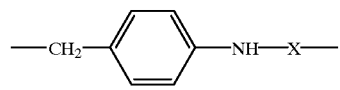
(IV)

wherein $R_3$ is a $C_1$–$C_{10}$ alkylene group, a $C_1$–$C_{10}$ alkylidene group or a $C_2$–$C_{10}$ alkenylene group, and X is a thiocarbonyl group or a group of the general formula

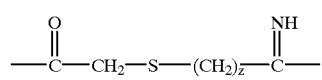
(V)

wherein z is 1–5.

* * * * *